US010420696B2

(12) United States Patent
Jang et al.

(10) Patent No.: US 10,420,696 B2
(45) Date of Patent: Sep. 24, 2019

(54) WALKING ASSISTANCE METHOD AND APPARATUSES PERFORMING THE SAME

(71) Applicant: Samsung Electronics Co., Ltd., Suwon-si, Gyeonggi-do (KR)

(72) Inventors: Jun-Won Jang, Seoul (KR); Kyung-Rock Kim, Yongin-si (KR); Youngbo Shim, Seoul (KR); Jusuk Lee, Hwaseong-si (KR); Bokman Lim, Yongin-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 788 days.

(21) Appl. No.: 14/982,680

(22) Filed: Dec. 29, 2015

(65) Prior Publication Data

US 2017/0027802 A1 Feb. 2, 2017

(30) Foreign Application Priority Data

Jul. 27, 2015 (KR) .......................... 10-2015-0105960

(51) Int. Cl.
*A61H 3/00* (2006.01)
*A61H 1/02* (2006.01)
*A61B 5/11* (2006.01)

(52) U.S. Cl.
CPC .............. *A61H 3/00* (2013.01); *A61B 5/112* (2013.01); *A61H 1/0244* (2013.01);
(Continued)

(58) Field of Classification Search
CPC ................ A61H 3/00; A61H 1/0244; A61H 2201/5084; A61H 2205/106; A61H 2205/10; A61H 2205/12; A61H 2201/5061; A61H 2201/501; A61H 2201/5005; A61H 2201/1676; A61H 2201/164; A61H 2201/1628; A61H 2201/5007; A61H 2003/007; A61H 2201/165;
(Continued)

(56) References Cited

U.S. PATENT DOCUMENTS

| 2007/0054777 A1* | 3/2007 | Kawai ..................... A61H 3/00 482/1 |
| 2008/0154165 A1* | 6/2008 | Ashihara ............... A61F 5/0102 602/23 |

(Continued)

FOREIGN PATENT DOCUMENTS

| JP | 2002301124 A | 10/2002 |
| JP | 2003135543 A | 5/2003 |

(Continued)

*Primary Examiner* — Quang D Thanh
(74) *Attorney, Agent, or Firm* — Harness, Dickey & Pierce, P.L.C.

(57) ABSTRACT

A walking assistance method may include: detecting a landing time of a foot of a user; and/or initiating gait assistance based on a first joint location of a first leg of the user sensed at the landing time and a second joint location of the user sensed after the landing time. A walking assistance apparatus may include: a driver configured to perform gait assistance of a user; and/or a controller configured to control the driver to initiate the gait assistance based on a first joint location of a first leg of the user sensed at a landing time of a foot of the user and a second joint location sensed after the landing time.

19 Claims, 13 Drawing Sheets

(52) U.S. Cl.
CPC ............... *A61B 2562/0219* (2013.01); *A61H 2003/007* (2013.01); *A61H 2201/164* (2013.01); *A61H 2201/165* (2013.01); *A61H 2201/1628* (2013.01); *A61H 2201/1676* (2013.01); *A61H 2201/501* (2013.01); *A61H 2201/5005* (2013.01); *A61H 2201/5007* (2013.01); *A61H 2201/5061* (2013.01); *A61H 2201/5069* (2013.01); *A61H 2201/5079* (2013.01); *A61H 2201/5084* (2013.01); *A61H 2205/06* (2013.01); *A61H 2205/065* (2013.01); *A61H 2205/10* (2013.01); *A61H 2205/106* (2013.01); *A61H 2205/108* (2013.01); *A61H 2205/12* (2013.01)

(58) Field of Classification Search
CPC ...... A61H 2205/108; A61H 2201/5069; A61H 2201/5079; A61B 5/112
See application file for complete search history.

(56) References Cited

U.S. PATENT DOCUMENTS

| | | |
|---|---|---|
| 2009/0131839 A1 | 5/2009 | Yasuhara |
| 2009/0270766 A1 | 10/2009 | Yasuhara |
| 2010/0094185 A1 | 4/2010 | Amundson et al. |
| 2011/0264015 A1* | 10/2011 | Endo ............... A61H 1/0255 601/35 |
| 2012/0101415 A1 | 4/2012 | Goffer et al. |
| 2012/0310122 A1 | 12/2012 | Endo et al. |
| 2014/0163435 A1 | 6/2014 | Yamamoto et al. |
| 2014/0212243 A1* | 7/2014 | Yagi ............... A61H 3/00 414/2 |
| 2014/0296761 A1 | 10/2014 | Yamamoto et al. |

FOREIGN PATENT DOCUMENTS

| | | |
|---|---|---|
| JP | 2013094305 A | 5/2013 |
| JP | 2013111368 A | 6/2013 |

* cited by examiner

WALKING ASSISTANCE METHOD AND APPARATUSES PERFORMING THE SAME

CROSS-REFERENCE TO RELATED APPLICATION(S)

This application claims priority from Korean Patent Application No. 10-2015-0105960, filed on Jul. 27, 2015, in the Korean Intellectual Property Office (KIPO), the entire contents of which are incorporated herein by reference.

BACKGROUND

1. Field

At least one example embodiment may relate generally to walking assistance methods. At least one example embodiment may relate generally to apparatuses performing the walking assistance methods.

2. Description of Related Art

With the onset of rapidly aging societies, many people may experience inconvenience and pain from joint problems, and interest in walking assistance apparatuses enabling the elderly or patients with joint problems to walk with less effort may increase. Furthermore, walking assistance apparatuses for intensifying muscular strength of human bodies may be useful for military purposes.

In general, walking assistance apparatuses may include body frames disposed on a trunk of a user, pelvic frames coupled to lower sides of the body frames to cover pelvises of the user, femoral frames disposed on thighs of the user, sural frames disposed on calves of the user, and/or pedial frames disposed on feet of the user. The pelvic frames and femoral frames may be connected rotatably by hip joint portions, the femoral frames and sural frames may be connected rotatably by knee joint portions, and/or the sural frames and pedial frames may be connected rotatably by ankle joint portions.

The users may wear the walking assistance apparatuses over the users' clothing.

Although some example embodiments will be described with relation to walking assistance methods and walking assistance apparatuses for humans, those skilled in the art will appreciate that some example embodiments may be applied to other types of methods, apparatuses, and systems, such as motion assistance methods and motion assistance apparatuses for animals, or more general purpose systems.

SUMMARY

Some example embodiments may provide walking assistance methods.

Some example embodiments may provide apparatuses performing walking assistance methods.

In some example embodiments, a walking assistance method may comprise: detecting a landing time of a foot of a user; and/or initiating gait assistance based on a first joint location of a first leg of the user sensed at the landing time and a second joint location of the user sensed after the landing time.

In some example embodiments, the initiating of the gait assistance may comprise: sensing first hip joint angle information corresponding to the first joint location of the user at the landing time; sensing second hip joint angle information corresponding to the second joint location of the user after the landing time; and/or initiating the gait assistance based on the first hip joint angle information and the second hip joint angle information.

In some example embodiments, the first hip joint angle information may comprise at least one of joint angle or joint angular velocity of a first hip joint.

In some example embodiments, the second hip joint angle information may comprise at least one of joint angle or joint angular velocity of a second hip joint.

In some example embodiments, the initiating of the gait assistance may comprise initiating output of an assist torque profile to assist a gait of the first leg of the user.

In some example embodiments, the initiating of the output may comprise: initiating output of a first assist torque profile to assist a gait of a right leg of the user; and/or initiating output of a second assist torque profile to assist a gait of a left leg of the user.

In some example embodiments, an output time of the first assist torque profile may differ from an output time of the second assist torque profile.

In some example embodiments, the detecting of the landing time may comprise detecting the landing time of the foot of the user based on acceleration information.

In some example embodiments, the method may further comprise: sensing a joint location of a second leg of the user when a hip joint cross occurs on both sides after the landing time; and/or terminating the output of the assist torque profile based on the joint location of the second leg of the user.

In some example embodiments, the method may further comprise: comparing a gait assistance duration set for a current step to a gait assistance proceeding time; and/or terminating the output of the assist torque profile based on a result of the comparing.

In some example embodiments, the gait assistance duration may be updated for each step based on a duration of a previous step.

In some example embodiments, a walking assistance apparatus may comprise: a driver configured to perform gait assistance of a user; and/or a controller configured to control the driver to initiate the gait assistance based on a first joint location of a first leg of the user sensed at a landing time of a foot of the user and a second joint location sensed after the landing time.

In some example embodiments, the apparatus may further comprise: a sensor configured to sense first hip joint angle information corresponding to the first joint location at the landing time, and/or configured to sense second hip joint angle information corresponding to the second joint location after the landing time.

In some example embodiments, the first hip joint angle information may comprise at least one of joint angle or joint angular velocity of a first hip joint.

In some example embodiments, the second hip joint angle information may comprise at least one of joint angle or joint angular velocity of a second hip joint.

In some example embodiments, the controller may be further configured to initiate output of an assist torque profile to assist a gait of the first leg of the user.

In some example embodiments, the controller may be further configured to initiate output of a first assist torque profile to assist a gait of a right leg of the user, and/or to initiate output of a second assist torque profile to assist a gait of a left leg of the user.

In some example embodiments, an output time of the first assist torque profile may differ from an output time of the second assist torque profile.

In some example embodiments, the controller may be further configured to detect the landing time based on acceleration information.

In some example embodiments, the controller may be further configured to terminate the output of the assist torque profile based on a joint location of a second leg of the user, the joint location being sensed when a hip joint cross occurs on both sides after the landing time.

In some example embodiments, the controller may be further configured to compare a gait assistance duration set for a current step to a gait assistance proceeding time, and/or to terminate the output of the assist torque profile based on a result of the comparing.

In some example embodiments, the gait assistance duration may be updated for each step based on a duration of a previous step.

BRIEF DESCRIPTION OF THE DRAWINGS

The above and/or other aspects and advantages will become more apparent and more readily appreciated from the following detailed description of example embodiments, taken in conjunction with the accompanying drawings, in which.

DETAILED DESCRIPTION

Figure 1:
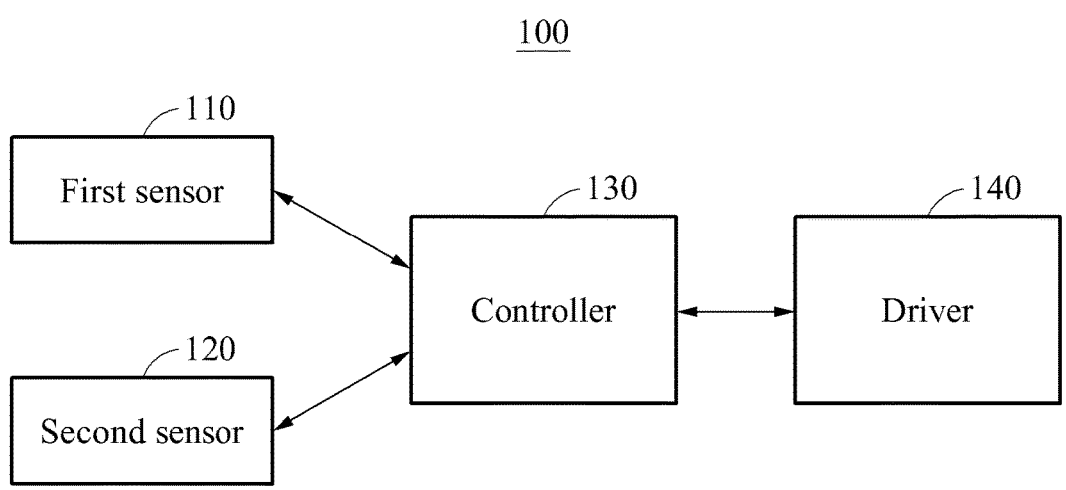
FIG. 1 is a block diagram illustrating a walking assistance apparatus according to at least one example embodiment.

Example embodiments will now be described more fully with reference to the accompanying drawings. Embodiments, however, may be embodied in many different forms and should not be construed as being limited to the embodiments set forth herein. Rather, these example embodiments are provided so that this disclosure will be thorough and complete, and will fully convey the scope to those skilled in the art. In the drawings, the thicknesses of layers and regions may be exaggerated for clarity.

It will be understood that when an element is referred to as being "on," "connected to," "electrically connected to," or "coupled to" to another component, it may be directly on, connected to, electrically connected to, or coupled to the other component or intervening components may be present. In contrast, when a component is referred to as being "directly on," "directly connected to," "directly electrically connected to," or "directly coupled to" another component, there are no intervening components present. As used herein, the term "and/or" includes any and all combinations of one or more of the associated listed items.

It will be understood that although the terms first, second, third, etc., may be used herein to describe various elements, components, regions, layers, and/or sections, these elements, components, regions, layers, and/or sections should not be limited by these terms. These terms are only used to distinguish one element, component, region, layer, and/or section from another element, component, region, layer, and/or section. For example, a first element, component, region, layer, and/or section could be termed a second element, component, region, layer, and/or section without departing from the teachings of example embodiments.

Spatially relative terms, such as "beneath," "below," "lower," "above," "upper," and the like may be used herein for ease of description to describe the relationship of one component and/or feature to another component and/or feature, or other component(s) and/or feature(s), as illustrated in the drawings. It will be understood that the spatially relative terms are intended to encompass different orientations of the device in use or operation in addition to the orientation depicted in the figures.

The terminology used herein is for the purpose of describing particular example embodiments only and is not intended to be limiting of example embodiments. As used herein, the singular forms "a," "an," and "the" are intended to include the plural forms as well, unless the context clearly indicates otherwise. It will be further understood that the terms "comprises," "comprising," "includes," and/or "including," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which example embodiments belong. It will be further understood that terms, such as those defined in commonly used dictionaries, should be interpreted as having a meaning that is consistent with their meaning in the context of the relevant art and should not be interpreted in an idealized or overly formal sense unless expressly so defined herein.

Reference will now be made to example embodiments, which are illustrated in the accompanying drawings, wherein like reference numerals may refer to like components throughout.

Figure 2:
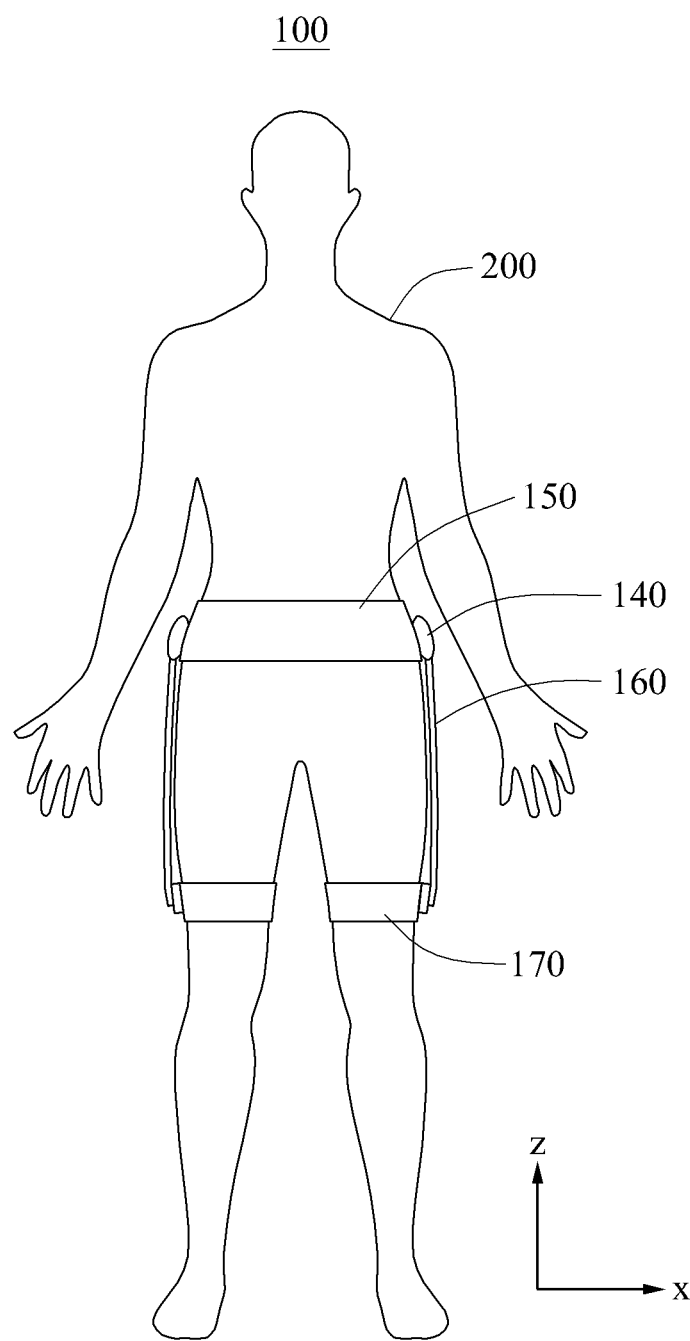
FIG. 2 is a front view illustrating a target body wearing the walking assistance apparatus of FIG. 1.
Figure 3:
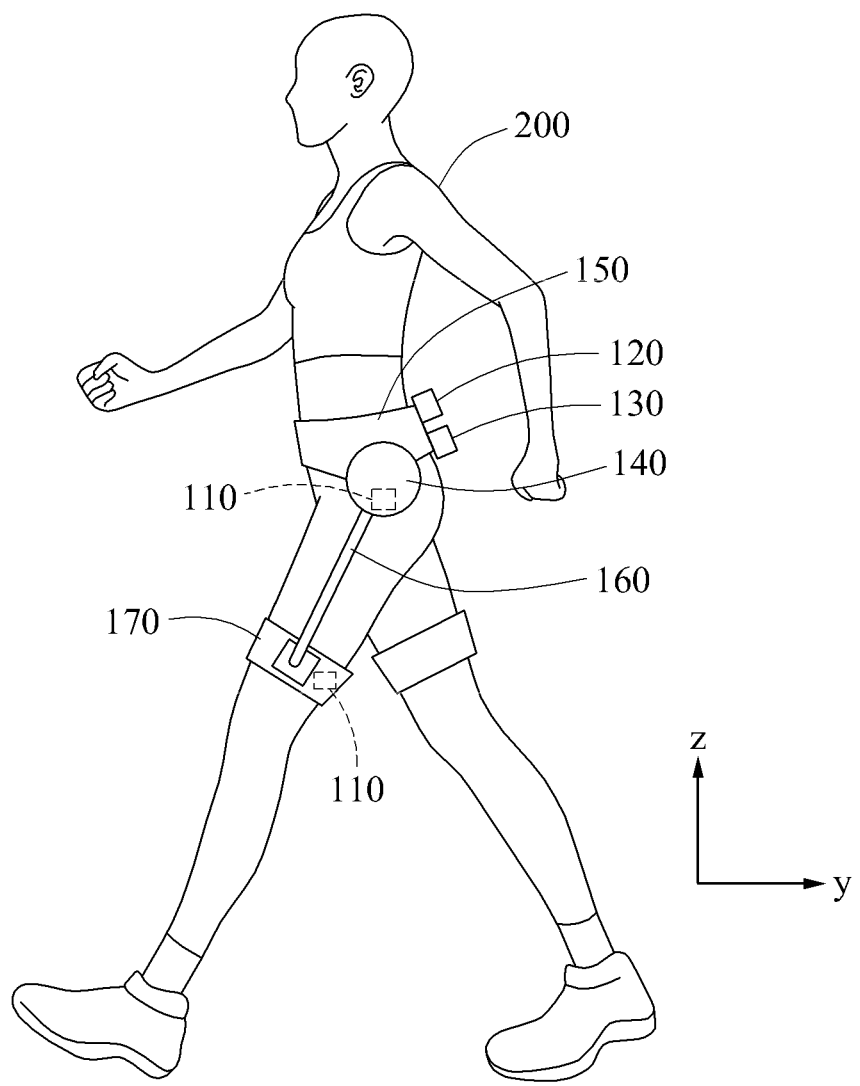
FIG. 3 is a side view illustrating a target body wearing the walking assistance apparatus of FIG. 1.

FIG. 1 is a block diagram illustrating a walking assistance apparatus 100 according to at least one example embodiment. FIG. 2 is a front view illustrating a target body wearing the walking assistance apparatus 100 of FIG. 1. FIG. 3 is a side view illustrating a target body wearing the walking assistance apparatus 100 of FIG. 1.

Referring to FIGS. 1 through 3, the walking assistance apparatus 100 may include a first sensor 110, a second sensor 120, a controller 130, and a driver 140. In the present disclosure, the term "walking" may be interchangeably used with the term "gait". Also, the walking assistance apparatus 100 may further include a fixing member 150, a force transmitting member 160, and a supporting member 170.

The walking assistance apparatus 100 may be worn by a target body, for example, a user 200, to assist a gait and/or a motion of the user 200. The target of object may be, for example, a person, an animal, or a robot, and an example of the target body is not limited thereto.

The walking assistance apparatus 100 may assist a gait and/or a motion of, for example, a hand, an upper arm, a lower arm, or another part of an upper body of the user 200. Alternatively, the walking assistance apparatus 100 may assist a gait and/or a motion of, for example, a foot, a calf, a thigh, or another part of a lower body of the user 200. Thus, the walking assistance apparatus 100 may assist a gait and/or a motion of a part of the user 200.

In some example embodiments, a walking assistance apparatus for a robot could establish a master/slave or slave/master relationship between the walking assistance apparatus and robot. Such a master device may not be a single device, but may include more than one device, each performing one or more functions of the master device (e.g., the functionality of the master device may be distributed). Similarly, the slave device may not be a single device, but may include more than one device, each performing one or more functions of the slave device (e.g., the functionality of the slave device may be distributed). Therefore, the functionality of the master device, the slave device, or the master and slave devices may be distributed.

In some example embodiments, in such master/slave or slave/master relationship, the master device may be required to perform certain functions, but may or may not perform other functions while maintaining its role as the master device. One or more of these other functions may be shared with or performed by the slave device (which maintains its role as the slave device). Similarly, the slave device may be required to perform certain functions, but may or may not perform other functions while maintaining its role as the slave device. One or more of those other functions may be shared with or performed by the master device (which maintains its role as the master device). Thus, the required functionality of the master and slave devices may be maintained, while functionality that may be shared with or performed by the other device may be so shared with or performed by the other device consistent with the master device maintaining its role as the master device and the slave device maintaining its role as the slave device.

Although FIG. 2 illustrates a case in which the walking assistance apparatus 100 is a two-sided embodiment, in some example embodiments, the walking assistance apparatus 100 may be a one-sided embodiment.

Although FIG. 2 illustrates a case in which the walking assistance apparatus 100 may assist a motion of both thighs of the user, in some example embodiments, the walking assistance apparatus 100 may also assist a motion of only one thigh of a user at a time.

The walking assistance apparatus 100 may detect a landing time of a foot of the user 200 while the user 200 makes a gait motion, and initiate gait assistance based on a first joint location and a second joint location. The gait motion may include a level walking, an ascending walking, for example, a walking slope-up, a descending walking, for example, a walking slope-down, and a standing motion.

The first joint location may be a joint location of one of legs of the user 200 sensed at the landing time, and the second joint location may be a joint location of one of the legs sensed after the landing time. The joint location may be a location of, for example a hip joint and a knee joint.

The walking assistance apparatus 100 may detect the landing time and initiate the gait assistance based on the first joint location sensed at the landing time and the second joint location sensed after the landing time. Through this, the walking assistance apparatus 100 may not initiate the gait assistance immediately after the foot of the user 200 lands on a ground. Also, the walking assistance apparatus 100 may protect the user 200 from a danger of gait assistance performed in an inverse direction in immediate response to an error, for example, fail and delay, in a stance phase enter recognition. Thus, the walking assistance apparatus 100 may provide gait assistance corresponding to an intent of the user 200 while the user 200 makes the gait motion.

Also, the walking assistance apparatus 100 may terminate the gait assistance.

Although FIGS. 2 and 3 illustrate the walking assistance apparatus 100 as, for example, a hip-type walking assistance apparatus, operating on a thigh of the user 200, the type of the walking assistance apparatus 100 is not limited thereto. The walking assistance apparatus 100 may assist a motion of another part of an upper body, for example, a hand, an upper arm, or a lower arm of the user, or a motion of another part of a lower body, for example, a foot, or a calf of the user. The walking assistance apparatus 100 may be applicable to, for example, a walking assistance apparatus that supports an entire pelvic limb, a walking assistance apparatus that supports a portion of a pelvic limb, and the like. The walking assistance apparatus that supports a portion of a pelvic limb may be applicable to, for example, a walking assistance apparatus that supports up to a knee, or a walking assistance apparatus that supports up to an ankle.

The first sensor 110 may sense joint locations of legs of the user 200 during a gait. For example, the first sensor 110 may sense both hip joint angular information corresponding to the joint locations. As illustrated in FIG. 3, the first sensor 110 may be included in at least one of the driver 140, the fixing member 150, and the supporting member 170.

For example, the both hip joint angular information may include at least one of angles of both hip joints, a difference in the angles of the hip joints, moving directions of the hip joints, and angular velocity information of the hip joints.

The first sensor 110 may wired or wirelessly transmit the both hip joint angular information to the controller 130.

The second sensor 120 may sense acceleration information and/or posture information while the user 200 is walking. For example, the second sensor 120 may sense at least one of x-axial, y-axial, and z-axial accelerations and x-axial, y-axial, and z-axial angular velocities. The second sensor 120 may be, for example, an inertial measurement unit (IMU) sensor. Although FIG. 3 illustrates the second sensor 120 implemented or mounted on a waist to which the fixing member 150 is attached, a location of the second sensor 120 is not limited thereto. Depending on an example. the second sensor 120 may be implemented or mounted, for example, on a shin, a thigh, or an ankle.

The second sensor 120 may wired or wirelessly transmit the acceleration information and/or the posture information to the controller 130.

The controller 130 may control an overall operation of the walking assistance apparatus 100. For example, the controller 130 may control the driver to output a force for assisting a gait of the user 200. The force may indicate, for example, an assistance torque.

The controller 130 may detect a landing time of a foot of the user 200 and control the driver 140 to initiate gait assistance based on a first joint location and a second joint location of the user 200. In this example, the controller 130 may initiate an output of an assist torque profile to assist the gait of the user 200.

Also, the controller 130 may control the driver 140 to terminate the gait assistance. In this example, the controller 130 may terminate the output of the assist torque profile. Descriptions related to a configuration and operation of the controller 130 will be provided as an example with reference to FIG. 4.

The driver 140 may be disposed on each of a left hip portion and a right hip portion of the user 200 to drive both hip joints of the user 200.

The driver 140 may generate an assistance torque to assist the gait of the user 200 under a control of the controller 130, for example, in response to an initiation of the output of the assist torque profile.

Also, the driver 140 may terminate or suspend the generating of the assistance torque under the control of the controller 130, for example, in response to a termination of the output of the assist torque profile.

The fixing member 150 may be attached to a part, for example, a waist of the user 200. The fixing member 150 may be in contact with at least a portion of an external surface of the user 200. The fixing member 150 may cover along the external surface of the user 200.

The force transmitting member 160 may be disposed between the driver 140 and the supporting member 170 to connect the driver 140 and the supporting member 170. The force transmitting member 160 may transmit the force received from the driver 140 to the supporting member 170. As an example, the force transmitting member 160 may comprise a longitudinal member such as, for example, a wire, a cable, a string, a rubber band, a spring, a belt, or a chain.

The supporting member 170 may support a target part, for example, a thigh of the user 200. The supporting member 170 may be disposed to cover at least a portion of the user 200. The supporting member 170 may apply a force to the target part of the user 200 using the force received from the force transmitting member 160.

Figure 4:
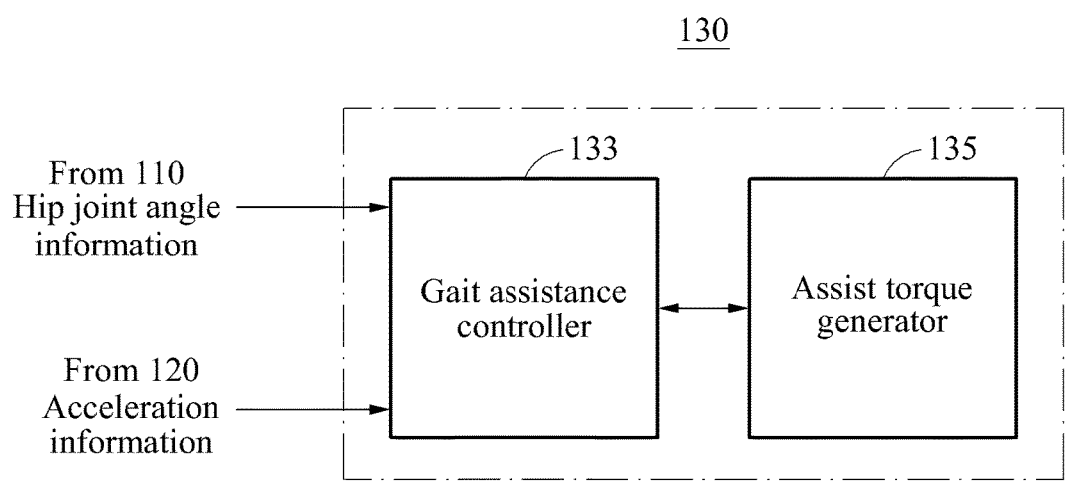
FIG. 4 is a block diagram illustrating a controller of FIG. 1.

FIG. 4 is a block diagram illustrating the controller 130 of FIG. 1.

Referring to FIGS. 1 through 4, the controller 130 may include a gait assistance controller 133 and an assist torque generator 135.

The gait assistance controller 133 may detect a landing time of a foot of the user 200 based on acceleration information transmitted from the second sensor 120.

The gait assistance controller 133 may detect the landing time of the foot of the user 200 based on the acceleration information, for example, a vertical acceleration, or a sum of squares of accelerations in an x-axial direction, a y-axial direction, and a z-axial direction corresponding to a vertical direction. Descriptions related to the gait assistance controller 133 detecting the landing time will also be provided with reference to FIG. 5.

The gait assistance controller 133 may receive hip joint angle information from the first sensor 110. In this example, the hip joint angle information may include first hip joint angle information corresponding to a first joint location of the user 200 and second hip joint information corresponding to a second joint location of the user 200. For example, the first joint location may be a joint location of one of both legs of the user 200 sensed at the landing time, and the second joint location may be a joint location of one of the legs sensed after the landing time.

The gait assistance controller 133 may control the assist torque generator 135 to initiate an output of an assist torque profile for gait assistance of the user 200 based on the first hip joint angle information and the second hip joint angle information.

The gait assistance controller 133 may control the assist torque generator 135 based on the first hip joint angle information, for example, a first hip joint angle $\theta_{fc}$, and the second hip joint angle information, for example, a second hip joint angle $\theta_{ai}$, as shown in Equation 1.

$$\theta_{ai} < \alpha \theta_{fc} \text{ or } \theta_{ai} < \theta_{fc} - \beta \ (\alpha <= 1, \beta >= 0) \qquad \text{[Equation 1]}$$

In Equation 1, $\alpha$ and $\beta$ denote weights, and may be differently set for each user. Also, $\alpha$ and $\beta$ may be differently set for each of a left leg and a right leg.

As an example, when the second joint location of the user 200 satisfies Equation 1, the gait assistance controller 133 may control the assist torque generator 135 to initiate the output of the assist torque profile for the gait assistance of the user 200.

The gait assistance controller 133 may control the assist torque generator 135 to terminate the output of the assist torque profile for the gait assistance of the user 200.

In an example, when a hip joint cross occurs after the landing time, the gait assistance controller 133 may receive the hip joint angle information from the first sensor 110. In this example, the hip joint angle information may include joint angle information corresponding to a leg differing from a reference leg between both legs of the user 200.

The gait assistance controller 133 may control the assist torque generator 135 to terminate the output of the assist torque profile for the gait assistance of the user 200 based on the hip joint angle information corresponding to the joint location, for example, the joint location of the differing leg.

As an example, when the hip joint angle is a threshold angle, the gait assistance controller 133 may control the output of the assist torque profile for the gait assistance of the user 200 to be terminated. Thus, when the hip joint cross occurs after the landing time, and when the joint location of the differing leg between both legs is a threshold location corresponding to the threshold angle, the gait assistance for the user 200 may be terminated.

As another example, the gait assistance controller 133 may compare a gait assistance duration set for a current step to a gait assistance proceeding time, and control the assist torque generator 135 to terminate the output of the assist torque profile for the gait assistance of the user 200.

When the gait assistance proceeding time is greater than or equal to the gait assistance duration, the gait assistance controller 133 may control the output of the assist torque profile for the gait assistance of the user 200 to be terminated.

The gait assistance proceeding time may indicate, for example, a time during which the gait assistance is initiated and performed. The gait assistance duration may be updated for each step based on a duration of a previous step.

Since the gait assistance controller 133 controls a termination of the gait assistance based on a gait assistance termination condition, for example, the threshold location of the joint and/or the gait assistance duration, the walking assistance apparatus 100 may be robust to a recognition error. Also, the walking assistance apparatus 100 may smoothly change a gait assistance direction in lieu of a sudden change in the gait assistance direction.

The assist torque generator 135 may generate the assist torque profile for the gait assistance of the user 200. For example, the assist torque profile may be generated and stored in a memory (not shown) in advance. In this example, the memory may be implemented internally or externally to the assist torque generator 135.

The assist torque generator 135 may initiate the output of the assist torque profile under a control of the gait assistance controller 133. For example, the assist torque generator 135 may initiate an output of a first assist torque profile to assist one of the left leg and the right leg of the user 200. The first assist torque profile may be, for example, one of an extension assist torque profile and a flexion assist torque profile. The assist torque generator 135 may initiate an output of a second assist torque profile to assist another one of the right leg and the left leg of the user 200. The second assist torque profile may be, for example, one of the extension assist torque profile and the flexion assist torque profile. An output time of the first assist torque profile may differ from an output time of the second assist torque profile.

The assist torque generator 135 may terminate the output of the assist torque profile under the control of the gait assistance controller 133.

Figure 5:
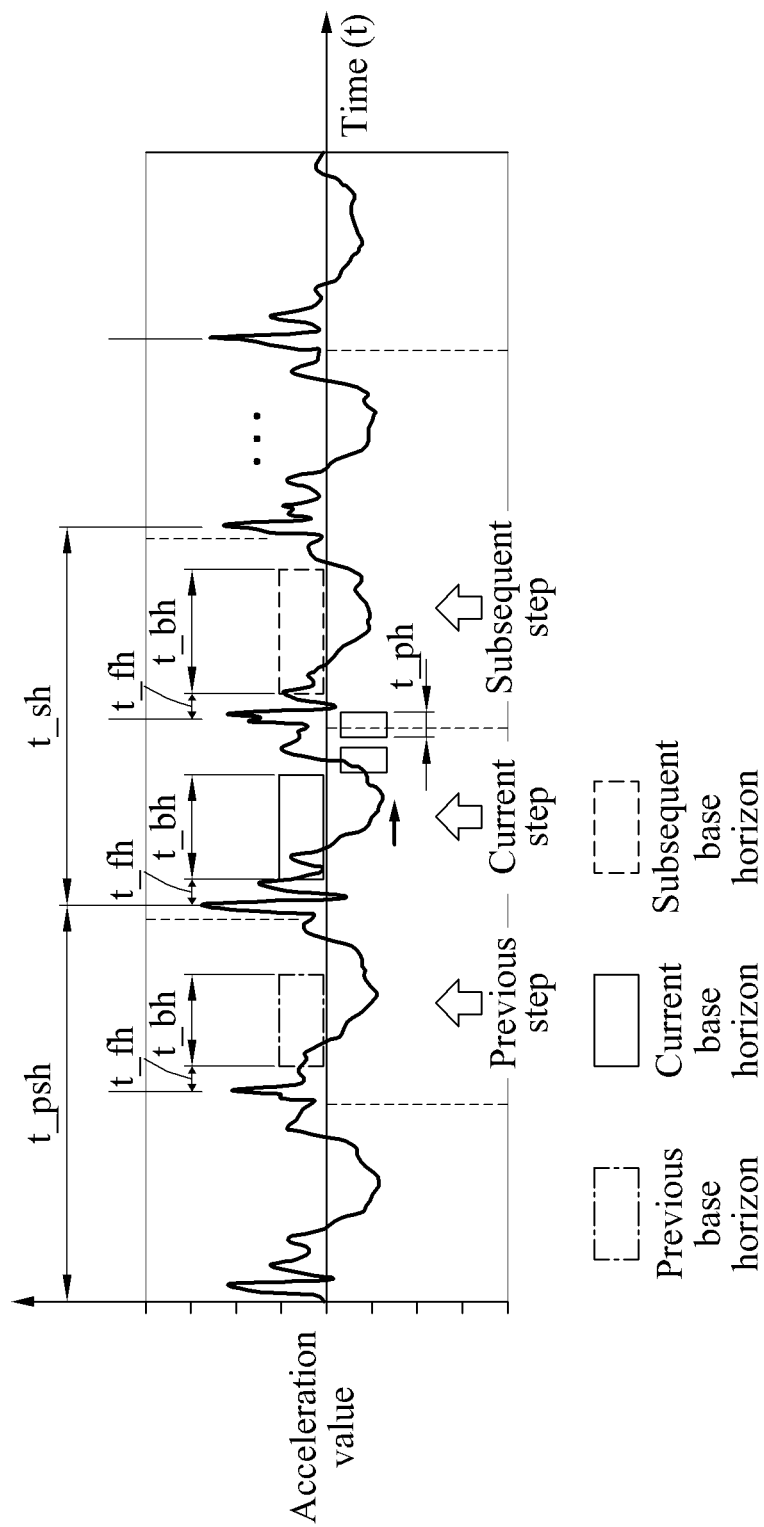
FIG. 5 is a graph illustrating a landing time detecting operation of a gait assistance controller according to at least one example embodiment.

FIG. 5 is a graph illustrating a landing time detecting operation of a gait assistance controller according to at least one example embodiment.

FIG. 5 illustrates intervals, for example, horizons, used to detect a landing time and an acceleration value acquired in the first sensor 110.

Referring to FIG. 5, t_psh denotes a previous stride horizon, and t_sh denotes a current stride horizon. t_bh denotes a base horizon, t_fh denotes a freeze horizon, and t_ph denotes a prediction horizon.

The base horizon may be a horizon in which a landing time does not occur in a previous step duration horizon. The base horizon may be set to be uniform for each step, or may be updated for each step based on a previous base horizon.

The base horizon may be set to follow the freeze horizon preset from a previous landing time to prevent an error in detection of the landing time after the landing time is detected. Reflecting that a desired time (that may or may not be predetermined) is physically required between the landing time and a subsequent landing time, the prediction horizon may be set to follow the base horizon.

A method of the gait assistance controller 133 detecting a landing time of a subsequent step based on a current step will be described. A horizon for the current step may be estimated using a horizon for a previous step. When a landing time of the current step is detected, a preset freeze horizon may be set from the landing time. As described above, the freeze horizon may be a horizon preset to prevent an error in detection of the landing time.

To detect the landing time of the subsequent step, the gait assistance controller 133 may compare a mean acceleration for the base horizon to a mean acceleration for a prediction horizon. The freeze horizon preset to prevent an error in detection of the landing time may be set to accurately set the mean acceleration for the base horizon estimated to be a horizon in which a landing time does not occur.

The current base horizon may be set based on a step duration horizon for the previous step. The horizon for the current step may be estimated based on the previous step duration horizon, and the base horizon may be set based on the estimated horizon for the current step.

For example, in detection of the landing time of the current step from the previous step, a difference between a mean acceleration for a previous base horizon and a mean acceleration for an initially set prediction horizon may be less than a threshold value. In this example, the prediction horizon may be shifted to detect the landing time by the gait assistance controller 133.

When a landing time is detected in the shifted prediction horizon, an actual duration horizon for the previous step estimated based on a step previous to the previous step may increase to an extent corresponding to a shifted portion of the prediction horizon. The horizon for the current step may be set based on the actual duration horizon for the previous step. Thus, the current base horizon may be updated to a horizon obtained by adding the shifted portion of the prediction horizon to the previous base horizon.

The prediction horizon may be shifted and set to follow the freeze horizon and the base horizon after the landing time of the current step occurs. The setting may be performed in advance, to allow the difference between the mean acceleration for the base horizon and the mean acceleration for the prediction horizon to be greater than or equal to the threshold value when the landing time occurs while the prediction horizon is minimized.

When the difference between the mean acceleration for the base horizon and the mean acceleration for the prediction horizon is greater than or equal to the threshold value, the gait assistance controller 133 may detect the prediction horizon as the landing time. For example, the gait assistance controller 133 may detect a point in time at which an acceleration is maximized in the prediction horizon as the landing time.

When the difference between the mean acceleration for the base horizon and the mean acceleration for the prediction horizon is less than the threshold value, the gait assistance controller 133 may determine that landing of the foot of the user does not occur in the prediction horizon.

In this example, the gait assistance controller 133 may shift the prediction horizon, and compare a difference between the mean acceleration for the base horizon and a mean acceleration for the shifted prediction horizon to the threshold value. The gait assistance controller 133 may detect the landing time by shifting the prediction horizon until the difference between the mean acceleration for the base horizon and the mean acceleration for the prediction horizon is greater than or equal to the threshold value.

When the landing time of the subsequent step is detected, the gait assistance controller 133 may store a final step duration horizon corresponding to an actual duration horizon for the current step. By storing the final step duration horizon for the current step, the gait assistance controller 133 may estimate a horizon for the subsequent step.

When a landing time of a step subsequent to the subsequent step is to be detected, the gait assistance controller 133 may estimate a duration horizon for the subsequent step through the stored final step duration horizon for the current step. In addition, a subsequent base horizon may also be updated based on the base horizon for the current step and the prediction horizon in which the landing time is detected.

As described above, the base horizon and the mean acceleration for the base horizon may be updated for each step. While the user 200 is walking, a step duration and an acceleration may vary. Thus, the gait assistance controller 133 may update a current base horizon and a mean acceleration for the current base horizon for each step through a previous step duration.

However, when a step duration and an acceleration of the user 200 do not have large deviations for each step, the base horizon and the mean acceleration for the base horizon may be set to be uniform values, thereby reducing a number of computations of the gait assistance controller 133.

A walking assistance apparatus supporting an entire pelvic limb of the user 200 may include a foot force sensor to detect the landing time of the foot of the user 200. Since the foot force sensor is mounted on a sole in the walking assistance apparatus supporting the entire pelvic limb, the landing time may be readily detected and, thus, the gait assistance controller 133 may not need to detect the landing time. The aforementioned walking assistance apparatus supporting a portion of the pelvic limb may not include the foot force sensor and, thus, the landing time may be detected by the gait assistance controller 133.

Figure 6:
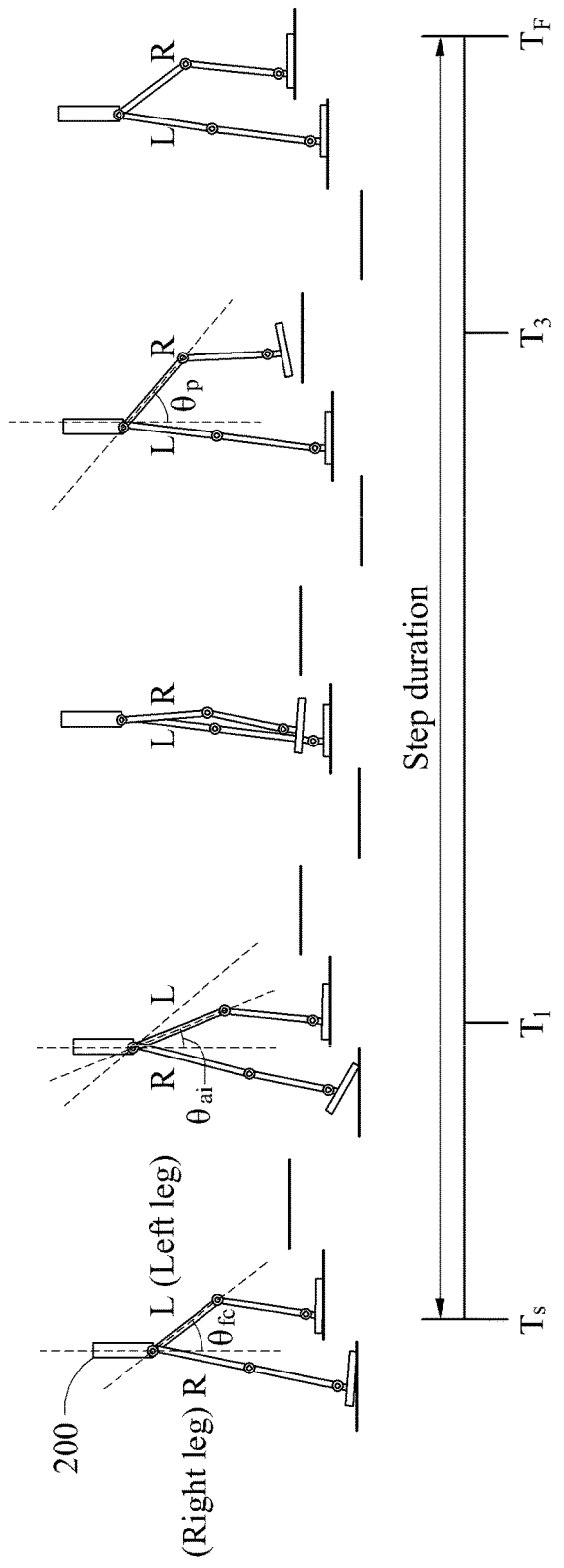
FIG. 6 illustrates an example of a gait assistance process for one step of a user according to at least one example embodiment.
Figure 7:
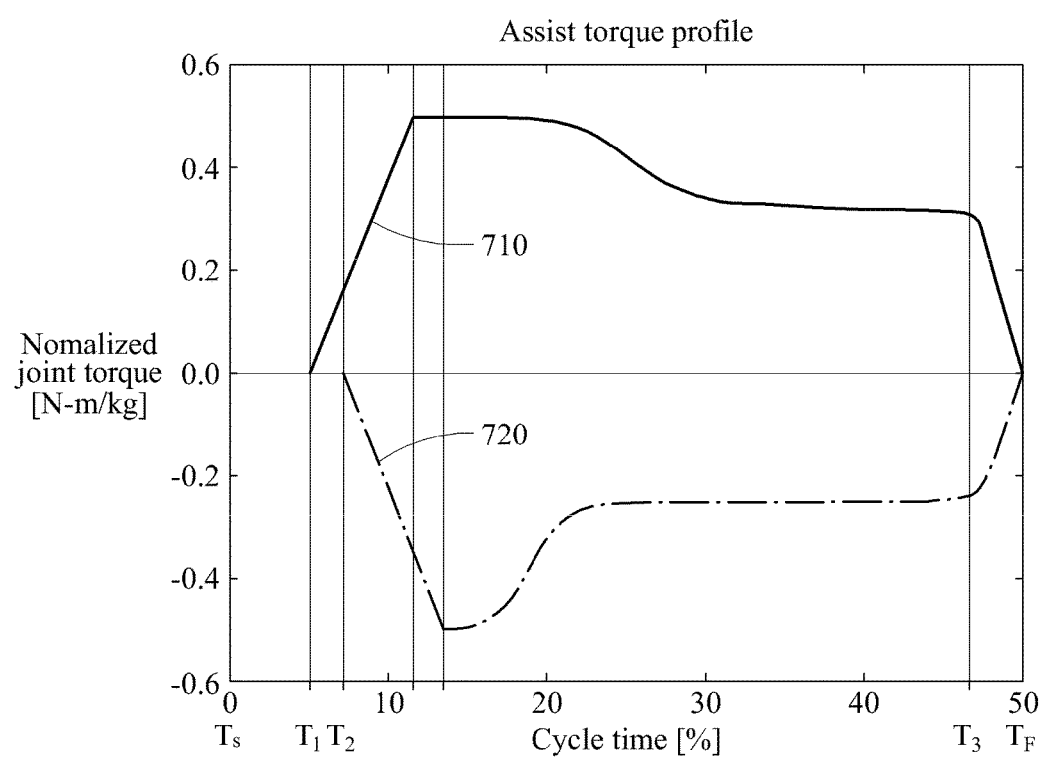
FIG. 7 illustrates an example of an assist torque profile corresponding to the gait assistance process of FIG. 6.

FIG. 6 illustrates an example of a gait assistance process for one step of a user according to at least one example embodiment. FIG. 7 illustrates an example of an assist torque profile (with normalized joint torque in Newton-meters per kilogram (N-m/kg) and cycle time expressed as a percentage of a time period between a landing time $T_s$ of a first leg and a time $T_f$ of terminating torque assist) corresponding to the gait assistance process of FIG. 6.

In FIG. 6, descriptions will be provided based on an example in which the user 200 performs an ascending walking, for example, a walking slope-up.

Referring to FIGS. 6 and 7, the gait assistance controller 133 may detect the landing time $T_s$ of a foot of the user 200.

The gait assistance controller 133 may receive a first hip joint angle $\theta_{fc}$ corresponding to a joint location of a left leg L sensed at the landing time $T_s$ from the first sensor 110. At a point in time $T_1$ after the landing time $T_s$, the gait assistance controller 133 may receive a second hip joint angle $\theta_{ai}$ corresponding to the sensed joint location of the left leg L from the first sensor 110.

When the second hip joint angle $\theta_{ai}$ satisfies Equation 1, the gait assistance controller 133 may control the assist torque generator 135 to initiate an output of an assist torque profile for gait assistance of the user 200.

The assist torque generator 135 may initiate an output of a first assist torque profile 710 to assist the left leg L at the point in time $T_1$. Also, the assist torque generator 135 may initiate an output of a second assist torque profile 720 to assist a right leg R at the point in time $T_1$.

Since the gait assistance controller 133 detects the landing time $T_s$ and controls gait assistance based on the first hip joint angle $\theta_{fc}$ sensed at the landing time $T_s$ and the second hip joint angle $\theta_{ai}$ sensed after the landing time $T_s$, the walking assistance apparatus 100 may not initiate the gait assistance immediately after the foot of the user 200 lands on a ground. For example, the walking assistance apparatus 100 may also initiate the gait assistance based on an intention of the user 200 when the user 200 steps a foot forward and halts during the walking slope-up, or when the user 200 resumes walking, for example, slowly walking slope-up, after standing still for a while.

At a point in time $T_3$ when a hip joint cross occurs on both sides after the landing time $T_s$, the gait assistance controller 133 may receive a hip joint angle $\theta_p$ corresponding to a joint location of the right leg R from the first sensor 110.

When the hip joint angle $\theta_p$ is a threshold angle, the gait assistance controller 133 may control the assist torque generator 135 to terminate the output of the assist torque profile for the gait assistance of the user 200.

Thus, the assist torque profile 135 may terminate the outputs of the first assist torque profile 710 and second assist torque profile 720 at the point in time $T_3$.

Figure 8:
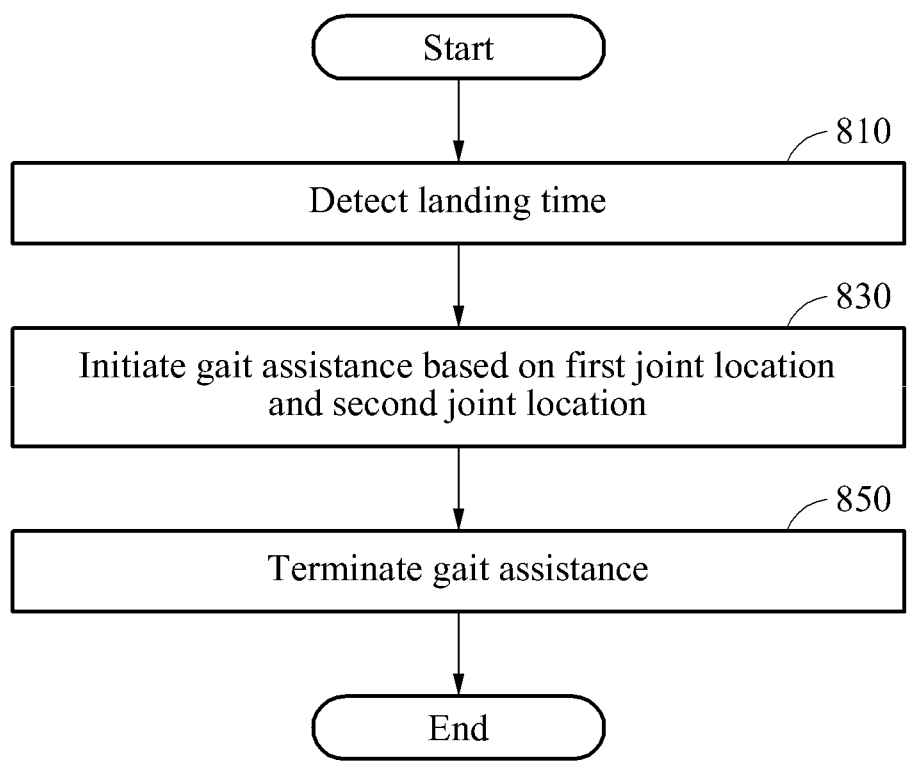
FIG. 8 is a flowchart illustrating an example of an operation method of the walking assistance apparatus of FIG. 1.

FIG. 8 is a flowchart illustrating an example of an operation method of the walking assistance apparatus 100 of FIG. 1.

Referring to FIG. 8, in operation 810, the walking assistance apparatus 100 may detect a landing time of a foot of the user 200.

In operation 830, the walking assistance apparatus 100 may initiate gait assistance based on a first joint location of one of both legs and a second joint location of one of the legs of the user 200. Before the gait assistance is initiated, the walking assistance apparatus 100 may sense the first joint location of one of the legs at a landing time. Also, the walking assistance apparatus 100 may sense the second joint location of one of the legs after the landing time. In this example, the aforementioned joint locations may indicate a location of, for example, a hip joint and a knee joint.

In operation 850, the walking assistance apparatus 100 may terminate the gait assistance.

Figure 9:
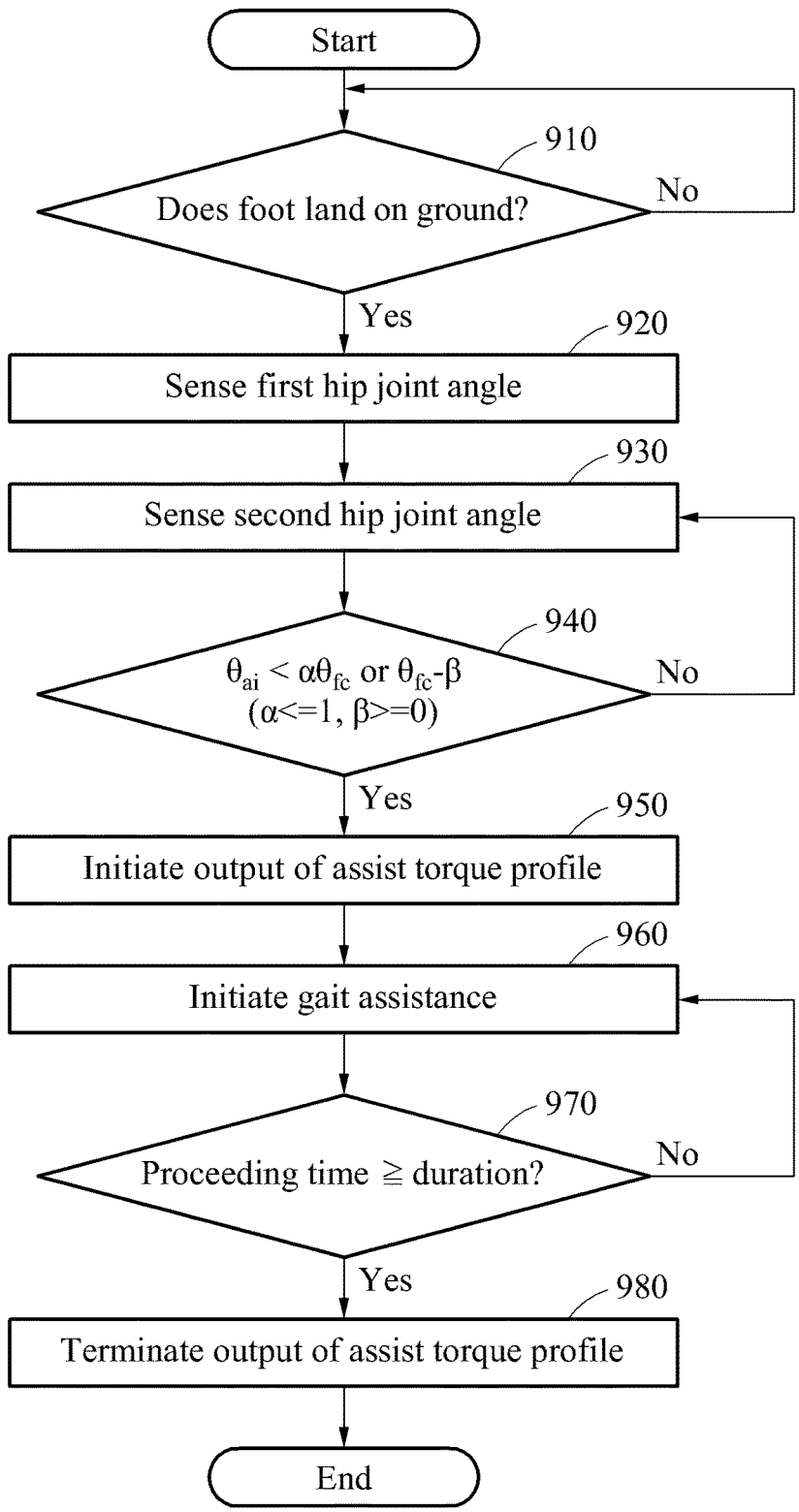
FIG. 9 is a flowchart illustrating another example of an operation method of the walking assistance apparatus of FIG. 1.

FIG. 9 is a flowchart illustrating another example of an operation method of the walking assistance apparatus 100 of FIG. 1.

Referring to FIG. 9, in operation 910, the controller 130 may determine whether a foot of the user 200 lands on a ground while the user 200 is walking. For example, the controller 130 may detect a landing time of the foot of the user 200.

In operation 920, the first sensor 110 may sense a first hip joint angle $\theta_{fc}$ corresponding to a first joint location of one of both legs of the user 200 at the landing time. The first sensor 110 may transmit the first hip joint angle $\theta_{fc}$ to the controller 130. In this example, the controller 130 may store the first hip joint angle $\theta_{fc}$ sensed at the landing time.

In operation 930, the first sensor 110 may sense a second hip joint angle $\theta_{ai}$ corresponding to a second joint location of one of the legs after the landing time. The first sensor 110 may transmit the second hip joint angle $\theta_{ai}$ to the controller 130.

In operation 940, the controller 130 may determine whether the second hip joint angle $\theta_{ai}$ satisfies Equation 1.

When the second hip joint angle $\theta_{ai}$ does not satisfy Equation 1, the controller 130 may receive the second hip joint angle $\theta_{ai}$ sensed after the landing time from the first sensor 110 in operation 930, and determine whether the second hip joint angle $\theta_{ai}$ satisfies Equation 1 in operation 940. Concisely, when the second hip joint angle $\theta_{ai}$ does not satisfy Equation 1, the controller 130 may perform operations 930 and 940 repetitively.

When the second hip joint angle $\theta_{ai}$ satisfies Equation 1, the controller 130 may initiate an output of an assist torque profile in operation 950. For example, the controller 130 may initiate an output of a first assist torque profile to assist one of the legs of the user 200. The controller 130 may initiate an output of a second assist torque profile to assist another one of the legs of the user 200. An output time of the first assist torque profile may differ from an output time of the second assist torque profile.

In operation 960, the driver 140 may initiate gait assistance for the user 200 under a control of the controller 130, for example, in response to an initiation of the output of the assist torque profile. For example, the driver 140 may generate an assistance torque for assisting the gait of the user 200.

In operation 970, the controller 130 may compare a gait assistance duration set for a current step to a gait assistance proceeding time. The gait assistance proceeding time may indicate, for example, a period of time during which gait assistance is initiated and performed. The gait assistance duration may be updated for each step based on a duration of a previous step.

When the gait assistance proceeding time is shorter than the gait assistance duration, the controller 130 may consistently output the assist torque profile to the driver 140 such that the driver 140 continuously assists the gait of the user 200 in operation 960.

When the gait assistance proceeding time is greater than or equal to the gait assistance duration, the controller 130 may terminate the output of the assist torque profile in operation 980. In response to a termination of the output of the assist torque profile, the driver 140 may terminate the gait assistance for the user 200. For example, the driver 140 may terminate or suspend the generating of the assistance torque.

Figure 10:
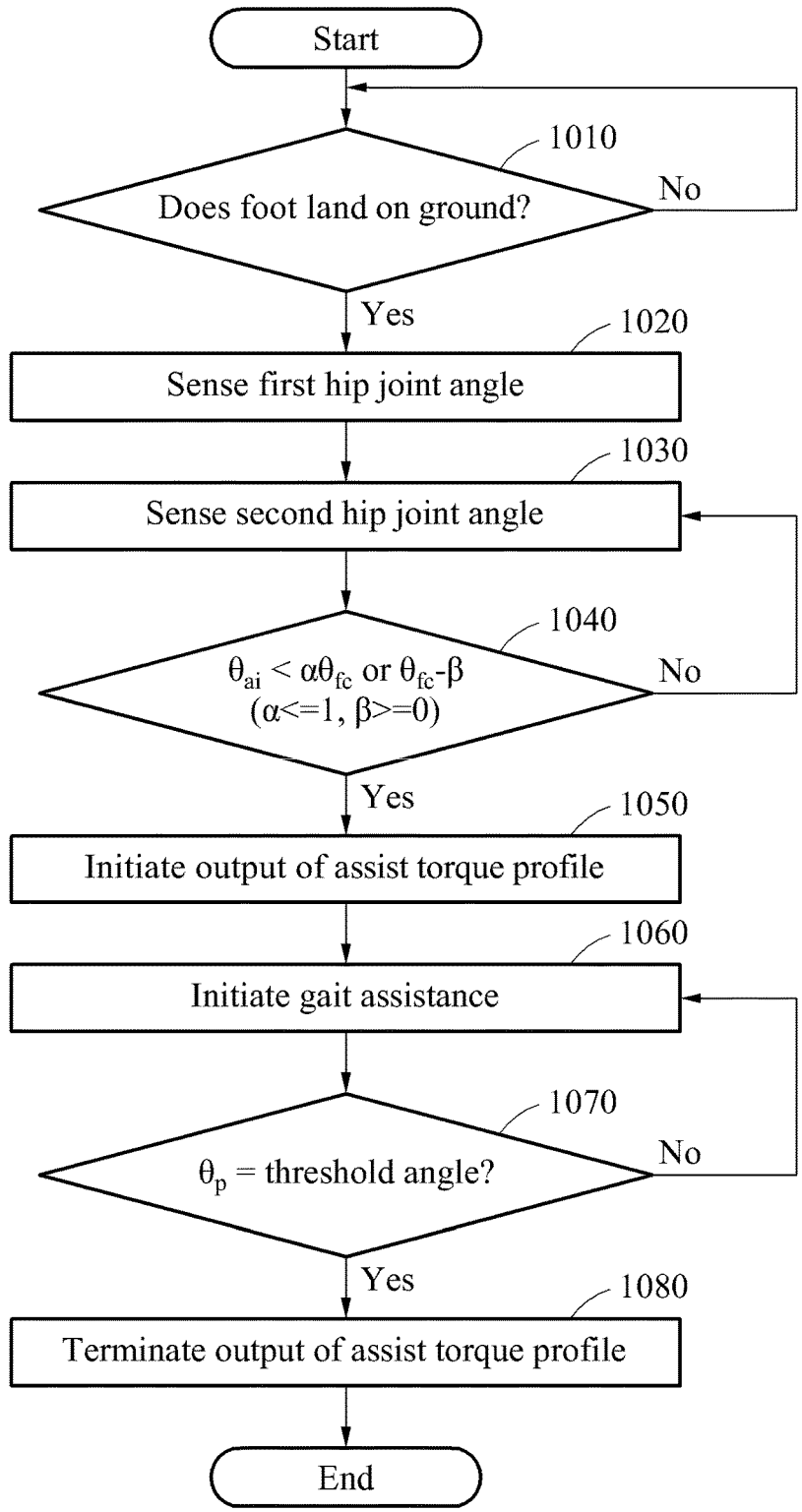
FIG. 10 is a flowchart illustrating still another example of an operation method of the walking assistance apparatus of FIG. 1.

FIG. 10 is a flowchart illustrating still another example of an operation method of the walking assistance apparatus 100 of FIG. 1.

Referring to FIG. 10, in operation 1010, the controller 130 may determine whether a foot of the user 200 lands on a ground while the user 200 is walking. For example, the controller 130 may detect a landing time of the foot of the user 200.

In operation 1020, the first sensor 110 may sense a first hip joint angle $\theta_{fc}$ corresponding to a first joint location of one of both legs of the user 200 at the landing time. The first sensor 110 may transmit the first hip joint angle $\theta_{fc}$ to the controller 130. In this example, the controller 130 may store the first hip joint angle $\theta_{fc}$ sensed at the landing time.

In operation 1030, the first sensor 110 may sense a second hip joint angle $\theta_{ai}$ corresponding to a second joint location of one of the legs after the landing time. The first sensor 110 may transmit the second hip joint angle $\theta_{ai}$ to the controller 130.

In operation 1040, the controller 130 may determine whether the second hip joint angle $\theta_{ai}$ satisfies Equation 1.

When the second hip joint angle $\theta_{ai}$ does not satisfy Equation 1, the controller 130 may receive the second hip joint angle $\theta_{ai}$ sensed after the landing time from the first sensor 110 in operation 1030, and determine whether the second hip joint angle $\theta_{ai}$ satisfies Equation 1 in operation 1040. Concisely, when the second hip joint angle $\theta_{ai}$ does not satisfy Equation 1, the controller 130 may perform operations 1030 and 1040 repetitively.

When the second hip joint angle $\theta_{ai}$ satisfies Equation 1, the controller 130 may initiate an output of an assist torque profile in operation 1050. For example, the controller 130 may initiate an output of a first assist torque profile to assist one of the legs of the user 200. The controller 130 may initiate an output of a second assist torque profile to assist another one of the legs of the user 200. An output time of the first assist torque profile may differ from an output time of the second assist torque profile.

In operation 1060, the driver 140 may initiate gait assistance for the user 200 under a control of the controller 130, for example, in response to an initiation of the output of the assist torque profile. For example, the driver 140 may generate an assistance torque for assisting the gait of the user 200.

In operation 1070, the controller 130 may compare a hip joint angle $\theta_p$. corresponding to the other one of the legs and sensed when a hip joint cross occurs after the landing time, to a threshold angle. For example, when the hip joint cross occurs after the landing time, the first sensor 110 may sense the hip joint angle $\theta_p$ corresponding to the other one of the legs and transmit the sensed hip joint angle $\theta_p$ to the controller 130.

When the hip joint angle $\theta_p$ differs from the threshold angle, the controller 130 may consistently output the assist torque profile to the driver 140 such that the driver 140 continuously assists the gait of the user 200 in operation 1060.

When the hip joint angle $\theta_p$ is equal to the threshold angle, the controller 130 may terminate the output of the assist torque profile in operation 1080. In response to a termination of the output of the assist torque profile, the driver 140 may terminate the gait assistance for the user 200. For example, the driver 140 may terminate or suspend the generating of the assistance torque.

Figure 11:
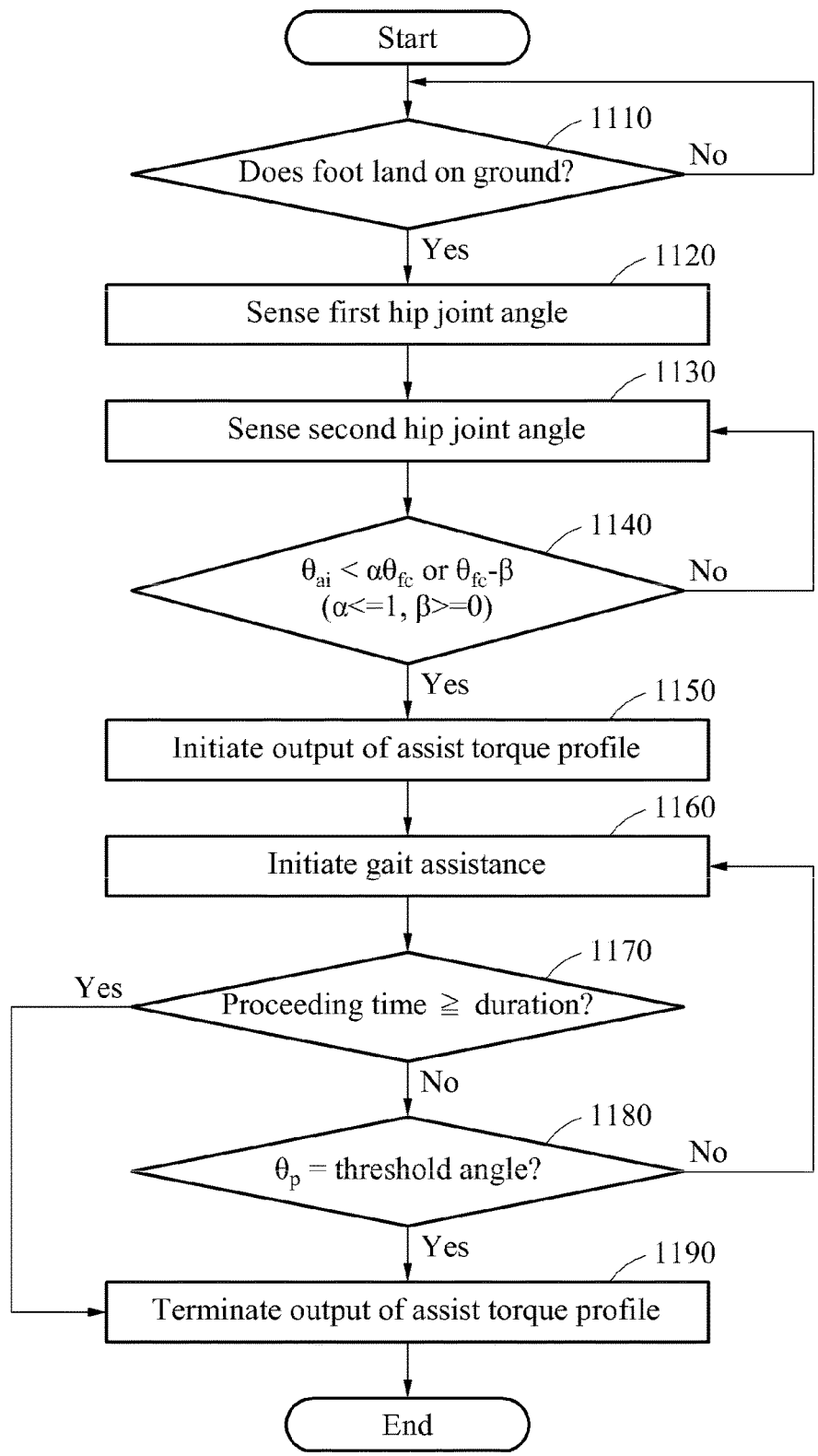
FIG. 11 is a flowchart illustrating yet another example of an operation method of the walking assistance apparatus of FIG. 1.

FIG. 11 is a flowchart illustrating yet another example of an operation method of the walking assistance apparatus 100 of FIG. 1.

Referring to FIG. 11, in operation 1110, the controller 130 may determine whether a foot of the user 200 lands on a ground while the user 200 is walking. For example, the controller 130 may detect a landing time of the foot of the user 200.

In operation 1120, the first sensor 110 may sense a first hip joint angle $\theta_{fc}$ corresponding to a first joint location of one of both legs of the user 200 at the landing time. The first sensor 110 may transmit the first hip joint angle $\theta^{fc}$ to the controller 130. In this example, the controller 130 may store the first hip joint angle $\theta_{fc}$ sensed at the landing time.

In operation 1130, the first sensor 110 may sense a second hip joint angle $\theta_{ai}$ corresponding to a second joint location of one of the legs after the landing time. The first sensor 110 may transmit the second hip joint angle $\theta_{ai}$ to the controller 130.

In operation 1140, the controller 130 may determine whether the second hip joint angle $\theta_{ai}$ satisfies Equation 1.

When the second hip joint angle $\theta_{ai}$ does not satisfy Equation 1, the controller 130 may receive the second hip joint angle $\theta_{ai}$ sensed after the landing time from the first sensor 110 in operation 1130, and determine whether the second hip joint angle $\theta_{ai}$ satisfies Equation 1 in operation 1140. Concisely, when the second hip joint angle $\theta_{ai}$ does not satisfy Equation 1, the controller 130 may perform operations 1130 and 1140 repetitively.

When the second hip joint angle $\theta_{ai}$ satisfies Equation 1, the controller 130 may initiate an output of an assist torque profile in operation 1150. For example, the controller 130 may initiate an output of a first assist torque profile to assist one of the legs of the user 200. The controller 130 may initiate an output of a second assist torque profile to assist another one of the legs of the user 200. An output time of the first assist torque profile may differ from an output time of the second assist torque profile.

In operation 1160, the driver 140 may initiate gait assistance for the user 200 under a control of the controller 130, for example, in response to an initiation of the output of the assist torque profile. For example, the driver 140 may generate an assistance torque for assisting the gait of the user 200.

In operation 1170, the controller 130 may compare a gait assistance duration set for a current step to a gait assistance proceeding time. The gait assistance proceeding time may indicate, for example, a period of time during which gait assistance is initiated and performed. The gait assistance duration may be updated for each step based on a duration of a previous step.

When the gait assistance proceeding time is greater than or equal to the gait assistance duration, the controller 130 may terminate the output of the assist torque profile in operation 1190. In response to a termination of the output of the assist torque profile, the driver 140 may terminate the gait assistance for the user 200. For example, the driver 140 may terminate or suspend the generating of the assistance torque.

When the gait assistance proceeding time is shorter than the gait assistance duration, the controller 130 may compare a hip joint angle $\theta_p$ corresponding to the other one of the legs and sensed when a hip joint cross occurs after the landing time, to a threshold angle in operation 1180. For example, when the hip joint cross occurs after the landing time, the first sensor 110 may sense the hip joint angle $\theta_p$ corresponding to the other one of the legs and transmit the sensed hip joint angle $\theta_p$ to the controller 130.

When the hip joint angle $\theta_p$ differs from the threshold angle, the controller 130 may consistently output the assist torque profile to the driver 140 such that the driver 140 continuously assists the gait of the user 200 in operation 1160.

When the hip joint angle $\theta_p$ is equal to the threshold angle, the controller 130 may terminate the output of the assist torque profile in operation 1190. In response to a termination of the output of the assist torque profile, the driver 140 may terminate the gait assistance for the user 200. For example, the driver 140 may terminate or suspend the generating of the assistance torque.

Figure 12:
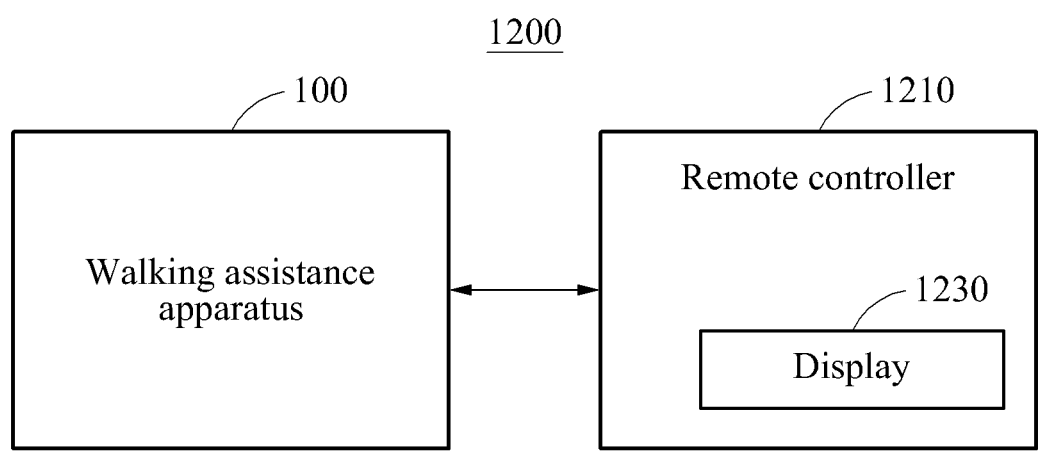
FIG. 12 is a block diagram illustrating an example of a walking assistance system according to at least one example embodiment.

FIG. 12 is a block diagram illustrating a walking assistance system 1200 according to at least one example embodiment.

Referring to FIG. 12, the walking assistance system 1200 may include the walking assistance apparatus 100 and a remote controller 1210.

The remote controller 1210 may control an overall operation of the walking assistance apparatus 100 in response to a user input. For example, the remote controller 1210 may initiate and suspend an operation of the walking assistance apparatus 100. Also, the remote controller 1210 may control an output of an assist torque profile to control gait assistance performed on the user 200 of the walking assistance apparatus 100.

The remote controller 1210 may include a display 1230. The display 1230 may be implemented as, for example, a touch screen, a liquid crystal display (LCD), a thin film transistor-liquid crystal display (TFT-LCD), a liquid emitting diode (LED) display, an organic LED (OLED) display, an active matrix OLED (AMOLED) display, and a flexible display.

The remote controller 1210 may provide a user interface (UI) and/or a menu corresponding to a function to manipulate the walking assistance apparatus 100 to the user 200 through the display 1230.

The display 1230 may display an operation status of the walking assistance apparatus 100 to be viewed by the user 200 under a control of the remote controller 1210.

Figure 13:
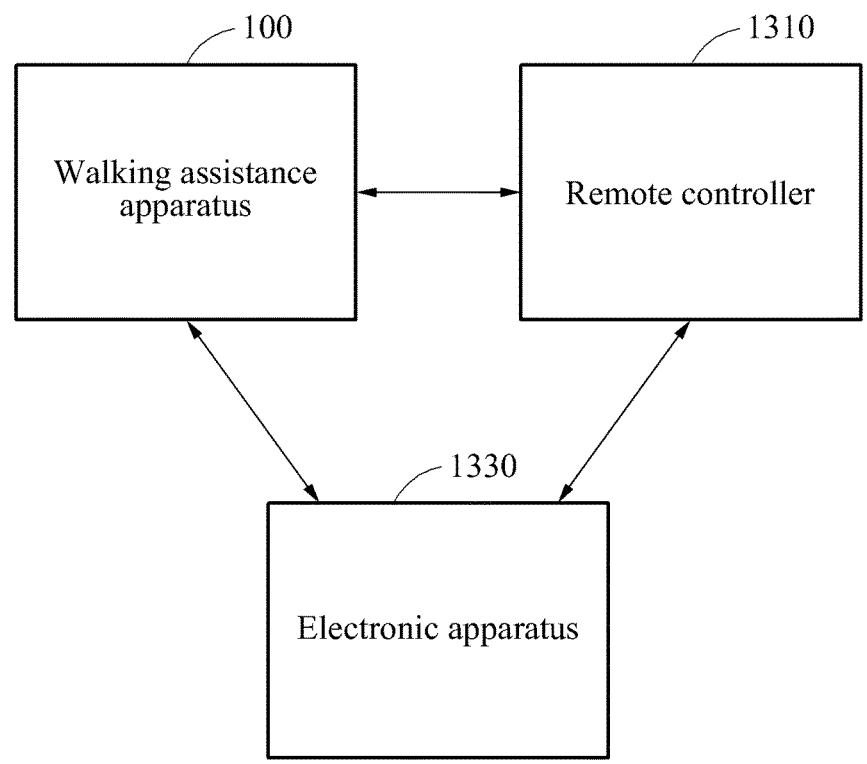
FIG. 13 is a block diagram illustrating another example of a walking assistance system according to at least one example embodiment.

FIG. 13 is a block diagram illustrating a walking assistance system 1300 according to at least one example embodiment.

Referring to FIG. 13, the walking assistance system 1300 may include the walking assistance apparatus 100 and a remote controller 1310, and an electronic apparatus 1330.

A configuration and an operation of the remote controller 1310 may be substantially the same as a configuration and an operation of the remote controller 1210 in FIG. 12.

The electronic apparatus 1330 may mutually communicate with the walking assistance apparatus 100 and/or the remote controller 1310. The electronic apparatus 1330 may sense a biosignal of the user 200 and transmit the sensed biosignal to the walking assistance apparatus 100 and/or the remote controller 1310.

The electronic apparatus 1330 may be implemented as, for example, a portable electronic device.

The portable electronic device may be implemented as, for example, a laptop computer, a mobile phone, a smartphone, a tablet PC, a mobile internet device (MID), a personal digital assistant (PDA), an enterprise digital assistant (EDA), a digital still camera, a digital video camera, a portable multimedia player (PMP), a personal navigation device or portable navigation device (PND), a handheld game console, an e-book, and a smart device.

The smart device may be implemented as, for example, a smart watch and a smart band.

Algorithms for implementation or control of the walking assistance technologies discussed in this application may be used for implementation or control of more general purpose apparatuses and/or methods of controlling apparatuses.

Methods for implementation or control of the walking assistance technologies discussed in this application may be written as computer programs and can be implemented in general-use digital computers that execute the programs using a computer-readable recording medium. In addition, a structure of data used in the methods may be recorded in a computer-readable recording medium in various ways. Examples of the computer-readable recording medium include storage media such as magnetic storage media (e.g., ROM (Read-Only Memory), RAM (Random-Access Memory), USB (Universal Serial Bus), floppy disks, hard disks, etc.) and optical recording media (e.g., CD-ROMs (Compact Disc Read-Only Memories) or DVDs (Digital Video Discs)).

In addition, some example embodiments may also be implemented through computer-readable code/instructions in/on a medium (e.g., a computer-readable medium) to control at least one processing element to implement some example embodiments. The medium may correspond to any medium/media permitting the storage and/or transmission of the computer-readable code.

The computer-readable code may be recorded/transferred on a medium in a variety of ways, with examples of the medium including recording media, such as magnetic storage media (e.g., ROM, floppy disks, hard disks, etc.) and optical recording media (e.g., CD-ROMs or DVDs), and transmission media such as Internet transmission media. Thus, the medium may be such a defined and measurable structure including or carrying a signal or information, such as a device carrying a bitstream according to some example embodiments. The media may also be a distributed network, so that the computer-readable code is stored/transferred and executed in a distributed fashion. Furthermore, the processing element could include a processor or a computer processor, and processing elements may be distributed and/or included in a single device.

In some example embodiments, some of the elements may be implemented as a 'module'. According to some example embodiments, 'module' may be interpreted as software-based components or hardware components, such as a field programmable gate array (FPGA) or an application specific integrated circuit (ASIC), and the module may perform certain functions. However, the module is not limited to software or hardware. The module may be configured so as to be placed in a storage medium which may perform addressing, or to execute one or more processes.

For example, modules may include components such as software components, object-oriented software components, class components, and task components, processes, functions, attributes, procedures, subroutines, segments of program code, drivers, firmware, microcodes, circuits, data, databases, data structures, tables, arrays, and variables. Functions provided from the components and the modules may be combined into a smaller number of components and modules, or be separated into additional components and modules. Moreover, the components and the modules may execute one or more central processing units (CPUs) in a device.

Some example embodiments may be implemented through a medium including computer-readable codes/instructions to control at least one processing element of the above-described embodiments, for example, a computer-readable medium. Such a medium may correspond to a medium/media that may store and/or transmit the computer-readable codes.

The computer-readable codes may be recorded in a medium or be transmitted over the Internet. For example, the medium may include a ROM, a RAM, a CD-ROM, a magnetic tape, a floppy disc, an optical recording medium, or a carrier wave such as data transmission over the Internet. Further, the medium may be a non-transitory computer-readable medium. Since the medium may be a distributed network, the computer-readable code may be stored, transmitted, and executed in a distributed manner. Further, for example, the processing element may include a processor or a computer processor, and be distributed and/or included in one device.

Although some example embodiments have been shown and described, it would be appreciated by those skilled in the art that changes may be made in these example embodiments without departing from the principles and spirit of the example embodiments, the scope of which is defined in the claims and their equivalents. For example, while certain operations have been described as being performed by a given element, those skilled in the art will appreciate that the operations may be divided between elements in various manners.

Although some example embodiments are described above with relation to walking assistance technologies, those skilled in the art will appreciate that some example embodiments may be applied to other types of systems, such as systems not used in the medical field (e.g., aerospace teleoperation systems, apparatuses for handling hazardous materials, patrol apparatuses, military apparatuses), humanoid apparatuses, or more general purpose control systems. Those skilled in the art will appreciate that the walking assistance technologies described in this application have a myriad of practical uses.

Although some example embodiments of the present disclosure have been shown and described, it would be appreciated by those skilled in the art that changes may be made in these example embodiments without departing from the principles and spirit of the invention, the scope of which is defined in the claims and their equivalents.

It should be understood that the example embodiments described herein should be considered in a descriptive sense only and not for purposes of limitation. Descriptions of features or aspects within each embodiment should typically be considered as available for other similar features or aspects in other embodiments.

What is claimed is:

1. A walking assistance method, comprising:
    detecting a landing time associated with a foot of a first leg of a user contacting a ground;
    sensing a joint angle of a first hip joint of the user at the landing time as first hip joint angle information, the first hip joint being associated with the first leg of the user;
    continually sensing the joint angle of the first hip joint of the user after the landing time as second hip joint angle information;
    determining whether the second hip joint angle information satisfies a condition; and
    initiating gait assistance in response to the second hip joint angle information satisfying the condition such that the gait assistance is delayed a duration of time after the landing time.

2. The walking assistance method of claim 1, wherein the first hip joint angle information and the second hip joint angle information include at least one of joint angle or joint angular velocity of the first hip joint.

3. The walking assistance method of claim 1, wherein the initiating of the gait assistance comprises:
    initiating output of an assist torque profile to assist a gait of the first leg of the user starting the duration of time after the landing time.

4. The walking assistance method of claim 3, wherein the initiating of the output comprises:
    initiating output of a first assist torque profile to assist a gait of the first leg of the user; and
    initiating output of a second assist torque profile to assist a gait of a second leg of the user.

5. The walking assistance method of claim 4, wherein an output duration of the first assist torque profile differs from an output duration of the second assist torque profile.

6. The walking assistance method of claim 1, wherein the detecting of the landing time comprises:
    detecting the landing time of the foot of the user based on acceleration information obtained from an acceleration sensor associated with a body of the user.

7. The walking assistance method of claim 3, further comprising:
    detecting whether the first leg of the user crosses a second leg of the user;
    continually sensing a joint angle of the second leg of the user when the first leg and the second leg cross after the landing time;
    determining whether the joint angle of the second leg of the user reaches a threshold angle after the first leg and the second leg cross; and
    terminating the output of the assist torque profile in response to the joint angle of the second leg of the user reaching the threshold angle.

8. The walking assistance method of claim 3, further comprising:
    comparing a gait assistance duration set for a current step to a gait assistance proceeding time; and
    terminating the output of the assist torque profile based on a result of the comparing.

9. The walking assistance method of claim 8, wherein the gait assistance duration is updated for each step based on the gait assistance duration of a previous step.

10. The walking assistance method of claim 1, wherein the second hip joint angle information satisfies the condition when the second hip joint angle is less than a weighted value of the first hip joint angle.

11. A walking assistance apparatus, comprising:
    a sensor;
    a driver configured to perform gait assistance of a user; and
    a controller configured to control the driver by,
        detecting a landing time associated with a foot of a first leg of the user contacting a ground, sensing a joint angle of a first hip joint of the user at the landing time as first hip joint angle information, the first hip joint being associated with the first leg of the user, continually sensing the joint angle of the first hip joint of the user after the landing time as second hip joint angle information, determining whether the second hip joint angle information satisfies a condition, and initiating the gait assistance in response to the second hip joint angle information satisfying the condition such that the gait assistance is delayed a duration of time after the landing time.

12. The walking assistance apparatus of claim 11, wherein the first hip joint angle information and the second hip joint angle information include at least one of joint angle or joint angular velocity of the first hip joint.

13. The apparatus of claim 11, wherein the controller is further configured to initiate output of an assist torque profile to assist a gait of the first leg of the user starting the duration of time after the landing time.

14. The walking assistance apparatus of claim 13, wherein the controller is further configured to, initiate output of a first assist torque profile to assist a gait of the first leg of the user, and to initiate output of a second assist torque profile to assist a gait of a second leg of the user.

15. The walking assistance apparatus of claim 14, wherein an output duration of the first assist torque profile differs from an output duration of the second assist torque profile.

16. The walking assistance apparatus of claim 11, further comprising an acceleration sensor associated with a body of the user, wherein the controller is further configured to detect the landing time based on acceleration information obtained from the acceleration sensor.

17. The walking assistance apparatus of claim 13, wherein the controller is further configured to, detect whether the first leg of the user crosses a second leg of the user, continually sense a joint angle of the second leg of the user when the first leg and the second leg cross after the landing time, determine whether the joint angle of the second leg of the user reaches a threshold angle after the first leg and the second leg cross, and terminate the output of the assist torque profile in response to the joint angle of the second leg of the user reaching the threshold angle.

18. The walking assistance apparatus of claim 13, wherein the controller is further configured to, compare a gait assistance duration set for a current step to a gait assistance proceeding time, and terminate the output of the assist torque profile based on a result of the comparing.

19. The walking assistance apparatus of claim 18, wherein the gait assistance duration is updated for each step based on the gait assistance duration of a previous step.

* * * * *